United States Patent
Lococo

Patent Number: 5,620,322
Date of Patent: Apr. 15, 1997

[54] DENTAL MATRIX STRIP

[76] Inventor: Michael Lococo, 5138 Valleyway, Niagara Falls, Ontario, Canada, L2E 1X1

[21] Appl. No.: 507,946

[22] Filed: Jul. 27, 1995

[51] Int. Cl.$^6$ ............................................. A61C 5/04
[52] U.S. Cl. ............................................................ 433/39
[58] Field of Search .................................... 433/39, 40

[56] References Cited

U.S. PATENT DOCUMENTS

| | | |
|---|---|---|
| 1,550,425 | 8/1925 | Burlew . |
| 2,196,896 | 4/1940 | Dvorak . |
| 2,646,622 | 7/1953 | Christie et al. . |
| 3,082,531 | 3/1963 | Jacobson . |
| 3,147,552 | 9/1964 | Goldman . |
| 3,383,769 | 5/1968 | Davis . |
| 3,421,222 | 1/1969 | Newman . |
| 3,510,948 | 5/1970 | Walthall . |
| 3,812,585 | 5/1974 | Balson . |
| 3,829,975 | 8/1974 | Balson . |
| 3,842,505 | 10/1974 | Eames ................................ 433/39 |
| 4,024,643 | 5/1977 | Eisenberg ........................... 433/39 |
| 4,117,596 | 10/1978 | Wallshein . |
| 4,500,288 | 2/1985 | von Weissenfluh ................. 433/40 |
| 4,553,937 | 11/1985 | Ropers ................................ 433/39 |
| 4,563,152 | 1/1986 | McClure ............................. 433/39 |
| 4,704,087 | 11/1987 | Dragan ............................... 433/39 |
| 4,726,768 | 2/1988 | Lee .................................... 433/34 |
| 4,824,365 | 4/1989 | von Weissenfluh ................. 433/40 |
| 4,909,736 | 3/1990 | Ritter ................................. 433/39 |
| 5,035,615 | 6/1991 | Din .................................... 433/39 |

FOREIGN PATENT DOCUMENTS

| | | | |
|---|---|---|---|
| 470552A | 2/1992 | European Pat. Off. ............ 433/39 |
| 0079728 | 5/1919 | Switzerland ....................... 433/39 |

Primary Examiner—Cary E. O'Connor
Attorney, Agent, or Firm—William A. Knoeller

[57] ABSTRACT

A dental matrix of the type of a flexible strip, preferably made from a thin, strong, flexible material such as Mylar™. Instead of the usual rectangular band, the strip tapers toward one end to provide a variety of sections having different width so that the overlap of a cavity, usually in the interproximal surface of a tooth, can be accurately made by simply sliding the strip to a desired position. As a result, there is an improved strength with which the strip envelopes the immediate vicinity of the filled cavity thus preventing undesired escape of the filling material towards the gum or towards the incisive part of the tooth. Two embodiments are disclosed.

9 Claims, 2 Drawing Sheets

DENTAL MATRIX STRIP

BACKGROUND OF THE INVENTION

The invention relates to a dental matrix of the type of a flexible sheet strip made preferably from a transparent material such as Mylar (™).

Matrixes of this type have been used for many decades as a tool for retaining a packed filling material in a tooth.

Various types of matrixes and different clamping devices for them have been suggested and described in prior art. Reference may be had, for instance to U.S. Pat. Nos. 4,909,736 (Ritter); 4,563,152 (McClure); 4,704,087 (Dragan); 4,824,365 (von Weissenfluh); 3,082,531 (Jacobson); 4,117,596 (Wallshein); 3,421,222 (Newman); 2,646,622 (Christie et al.); 2,196,896 (Dvorak) and many other references.

Despite a large number of various types of the matrixes and their clamping mechanisms, today's practitioners prefer, by and large, a flexible strip of Mylar™ which is preferred for the inherent strength of the material and relatively low manufacturing costs. A typical matrix strip is a rectangular band about ½ inch wide, approximately 4 inches long and about 0.001" thick. Most practitioners prefer to apply the strip and to manually hold it in place until the respective filling settles.

One of the problems with all types of the known strips is that they are difficult to conform exactly to the shape of the tooth as in most cases the width of the matrix is selected to extend over the entire height of an average human tooth. This arrangement often results in escape of some of the packed filling material above or below the applied matrix, hardening at points from which it has to be subsequently removed, for instance near the gums or on the incisive part of a tooth. There are known matrixes of this type where the width of the band is smaller than the height of the tooth. The drawback of this band is in that often it is of insufficient width to cover the entire surface of the filling packed in a cavity.

Thus, the practitioner usually maintains a supply of matrix bands of different widths to match the particular size requirement.

The flexible strip-like matrix is typically applied around at least about 75% of the periphery of the respective tooth. This results in that the strip has to be positioned between proximal tooth surfaces. It is not uncommon that interproximal surfaces of two adjacent teeth abut firmly against each other leaving only a small gap at the gingival interproximate portion at which the proximal surfaces are spaced apart. This often gives rise to difficulties in inserting the matrix as the strip has to be forced interproximate the teeth from their incisal edge toward the gingival part of the interproximate portion.

SUMMARY OF THE INVENTION

It is an object of the present invention to advance the art of the matrixes described above by providing a matrix which is simple in structure and thus inexpensive to produce and which is capable of firmly engaging the tooth closely about the packed filling, while the occurrence of an overflow of the filling material to undesired locations is at least reduced and often eliminated. It is also an object of the present invention to provide a matrix which is relatively easily applicable between proximal tooth surfaces in instances where the proximal surfaces are not sufficiently spaced.

In general terms, the invention provides a dental matrix strip of thin, flexible material comprising a major end portion; a minor end portion; a first side edge portion extending between said end portions; a second side edge portion extending between said end portions; at least a part of the second side edge portion being convergent with respect to the first side edge portion in a direction from said major end portion to said minor end portion.

In a particularly preferred embodiment, and still defining the invention in general terms, the second side edge portion includes a convergent section extending from said major end portion, over a major part of the length of the strip, and a parallel section disposed at an obtuse angle with an end of the convergent section remote from said major end portion. The parallel section is generally parallel with the first side edge portion and extending over a minor part of the length of the strip. The width of the strip at said minor part of the length of the strip is uniform and is smaller than the usual height of the gingival section of a proximal surface of a human tooth. Thus, the minor part forms a leader which facilitates the insertion of the matrix strip into a position interproximate of adjacent teeth.

BRIEF DESCRIPTION OF THE DRAWINGS

The invention will be described by way of two embodiments, with reference to the accompanying diagrammatic, not-to-scale drawings, wherein.

DETAILED DESCRIPTION

Figure 1:
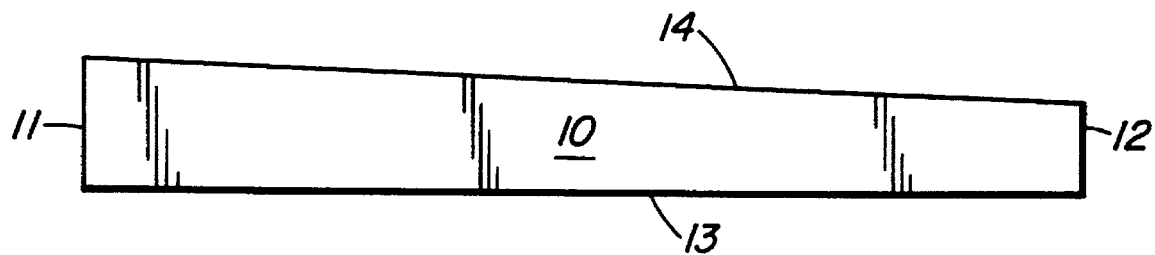
FIG. 1 is a plan view of an exemplary first embodiment of the matrix.

Reference may now be had to FIG. 1. It shows the first prototype of the present invention.

The matrix is a transparent strip 10 made from Mylar™ a trademark of E.I. Du Pont de Nemours and Company, for a polyester film and flexible film and having a major end portion 11, an opposed minor end portion 12, a first side portion 13 which defines the base of the quadrangular contour in the illustration, and an opposed second side portion 14 which is convergent with the first side portion 13 in the direction from the major end portion 11 to the minor end portion 12.

The width at the major end portion 11 is about ½ inch. It tapers to about ⅜ inch at the minor end portion 12. The length of the first side portion 13 (and thus of the strip) is about 4 inches. The thickness of the strip is about 0.001", as is usual with known Mylar™ matrix strips presently in use.

It will be appreciated that the width at the major end of about ½ inch presents a measurement which is slightly more than the normal height of a human tooth as a distance from the incisal edge to the gum, while the width at the minor end portion 12 is less than the usual minimum diameter of a cavity which has been excavated of the lesion and packed with a filling material.

Figure 2:
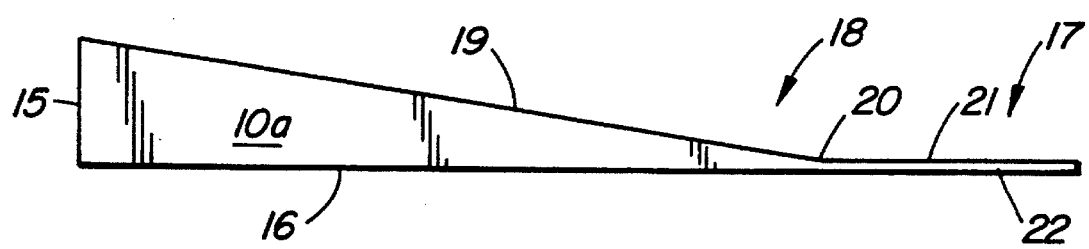
FIG. 2 is a plan view similar to that of FIG. 1 but showing an exemplary second embodiment of the matrix.

Turning now to the embodiment of FIG. 2, this matrix strip 10a is made from the same material as described with respect to FIG. 1. However, the shape and some measurements have been changed.

In particular, the major end portion 15 has the same size as the major end portion 11. Also, the first side portion 16 is similar in shape and length (about 4 inches) to the first side portion 13 of the first embodiment.

However, the shape of the strip at the second end portion 17, disposed opposite to the major end portion 15, is substantially different from FIG. 1. The second side portion 18 displays two linear sections: a convergent or tapering section 19 extends from said major end portion 15, over about 3 inches of the overall length as measured on the first side portion 16, from the major end portion 15. The tapering section 19 merges, at an obtuse angled corner 20, with a shorter parallel section 21. As FIG. 2 shows, the parallel section 21 is generally parallel with the first side edge portion 16. It is located at a small distance of about 1/32 inch from the first side portion 16 to define a leader 22 integral with the reset of the strip. The leader 22 is about 1 inch long. The width of about 1/32 inch is selected as a width smaller than the normal height of free space between gingival sections of interproximate surfaces.

The second embodiment shown in FIG. 2 is believed to be superior to the first embodiment as it provides, in addition to the capability of more exactly selecting the overlap by the matrix of a packed cavity, an easier inserting of the matrix between adjacent teeth that do not provide sufficient interproximate space.

Figure 3:
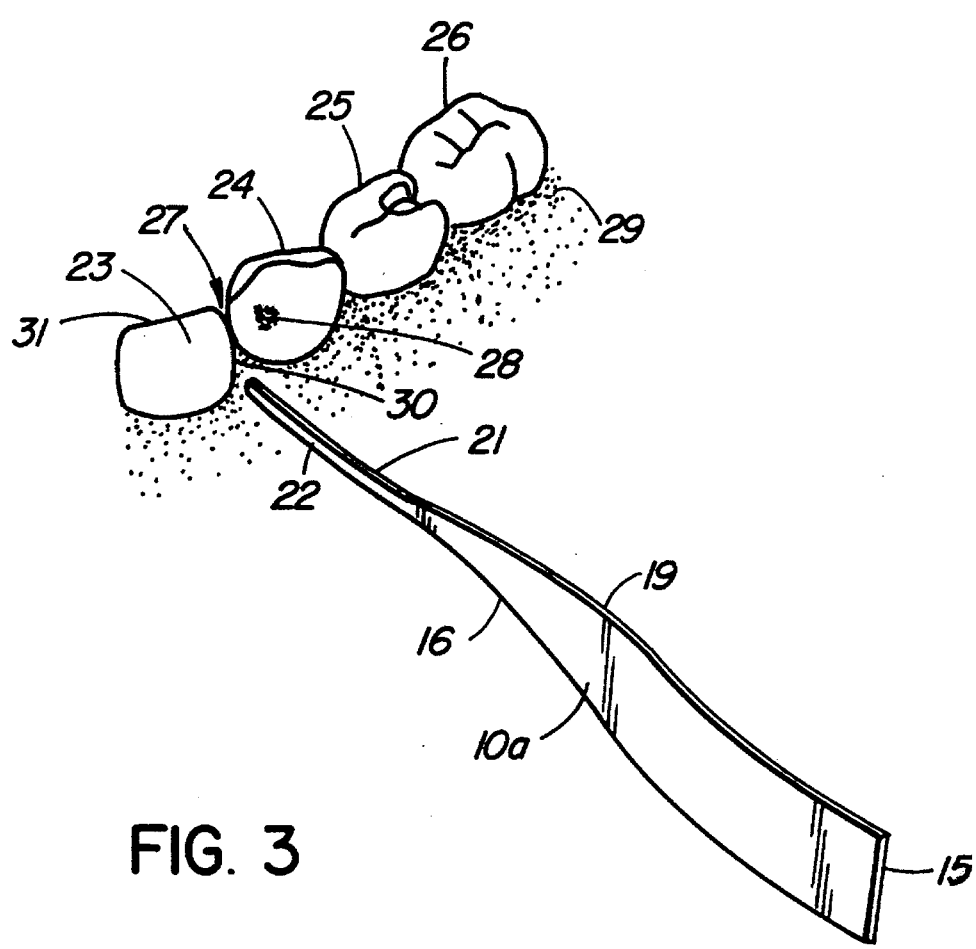
FIG. 3 is a simplified perspective view showing a first stage of inserting the matrix into the interproximate space.

Turning now to FIG. 3, the illustration diagrammatically depicts a number of teeth 23, 24, 25, 26. The arrow 27 points to an interproximal space. The tooth 24 is shown with a cavity 28 which has been excavated of lesion and is ready to be packed with a filling material. The interproximal surfaces of teeth 23, 24 abut against each other at points remote from the gum 29, leaving a low free interproximate gingival space 30 which is generally coincident with the gingival margins of the teeth 23, 24 as is well known.

Figure 4:
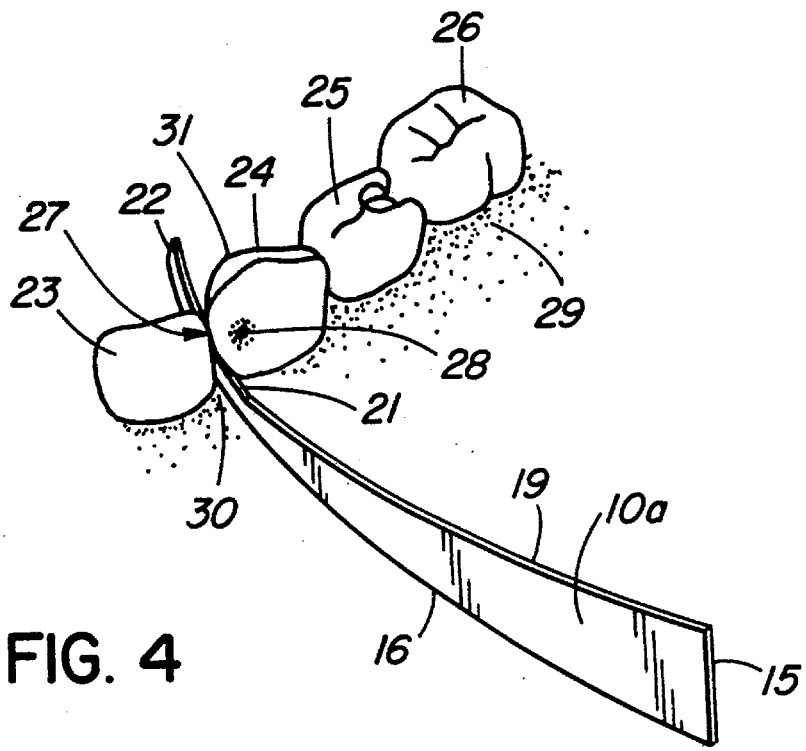
FIG. 4 is similar to that of FIG. 3 but shows the next stage of inserting the matrix into the interproximate space.
Figure 5:
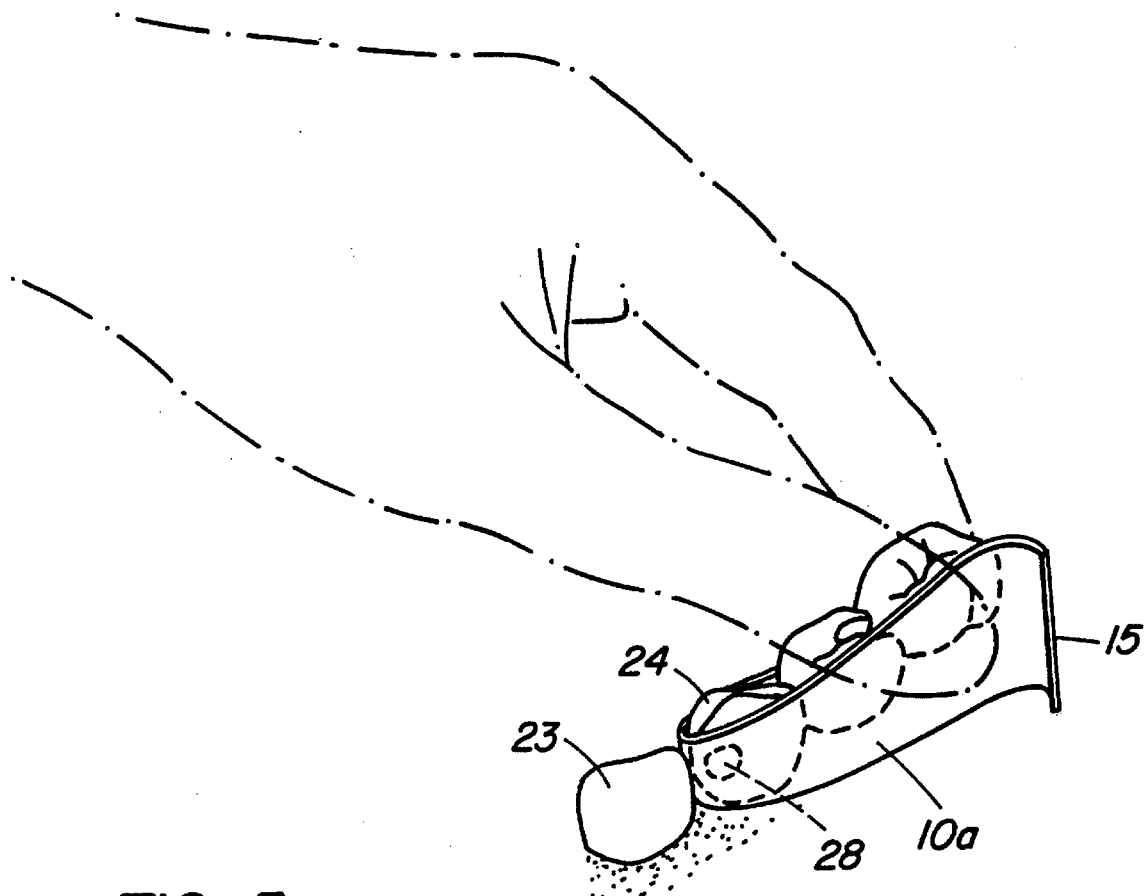
FIG. 5 shows the matrix in place, overlapping a cavity filled with a packed filling material.

In operation, the leader 22 is inserted (FIG. 4) into the gingival space 30 with the first side portion 16 adjacent to the gum 29 and with the parallel section 21 turned toward the incisal edges 31 of the teeth 24, 25. The leader is pulled through the gingival space 30 until the tapering section 19 begins to penetrate the interproximal space 27 slightly forcing the adjacent teeth 23, 24 apart to permit the sliding of the strip 10a through the interproximal space thus made. The practitioner pulls the strip 10a until such time as the gradually increased width or spacing between the edges 19 and 16 is sufficient to slightly overlap the entire cavity 28. The cavity 28 is then filled and packed with a filling material and is slightly overfilled. Then the strip 10a is tightly wrapped around the tooth 24 to smoothen the surface of the packed filling material, holding the strip until the filling material is cured.

Due to the minimum but sufficient overlap of the cavity 28 with the strip, the strip more precisely envelopes the surface of the tooth 24 surrounding the cavity than in prior art strips where the strips were usually substantially wider than required or where the size had to be selected from a plurality of different sizes of matrixes.

The holding of the strip 10a over the curing filling material is preferably manual which is not to say that a suitable clamping means for the matrix of the present invention could not be developed for this purpose. Known structures could be adapted for this purpose. They are shown in numerous prior art references. These include, as few examples only, in U.S. Pat. Nos. 3,147,582 (Goldman), 4,704,087 (Dragan), 4,824,365 (von Weissenfluh); or 4,909,736 (Ritter), the disclosures of the said patents being incorporated herein by reference.

It can be seen from the above that the present invention provides, by a simple modification, a new and useful dental matrix which improves and facilitates the use of same while retaining a simple structure resulting in low manufacturing costs.

Those skilled in the art will readily appreciate that many modifications of the structure of the matrix of the present invention, differing from the embodiment shown in material, in physical configuration or in size can be developed without departing from the scope of the present invention. I therefore wish to protect by letters patent issued on this application all such embodiments which fairly fall within the scope of my contribution to the art.

I claim:

1. An elongated dental matrix strip of thin, flexible material comprising:
   (a) a major width end portion;
   (b) a minor width end portion;
   (c) a first side edge portion extending longitudinally between said end portions;
   (d) a second side edge portion extending longitudinally between said end portions;
   (e) said second side edge portion being convergent at an acute angle with respect to the first side edge portion in a direction from said major end portion to said minor end portion.

2. The dental matrix strip as recited in claim 1, wherein the width of the strip at said major end portion is about equal to the height of an average human tooth and wherein the overall length of the strip is about 4 inches.

3. The dental matrix strip as recited in claim 2, wherein the width of the strip at said major end portion is about ½ inch.

4. The dental matrix as recited in claim 3, wherein the width of the strip at the minor end portion is about ¼ inch.

5. The dental matrix as recited in claim 1, wherein the second side edge portion includes
   (a) a convergent section extending from said major end portion, over a major part of the length of the strip, and
   (b) a parallel section,
   (c) said parallel section being disposed at an obtuse angle with an end of the convergent section remote from said major end portion;
   (d) said parallel section being generally parallel with the first side edge portion and extending over a minor part of the length of the strip;
   (e) the width of the strip at said minor part of the length of the strip being uniform and being smaller than the usual height of the gingival section of a proximal surface of a human tooth; whereby said minor part forms a leader for facilitating the insertion of the matrix strip into a position interproximate of adjacent teeth.

6. The dental matrix as recited in claim 5, wherein the width of said minor part of the length of the strip is about 1/16 inch.

7. The dental matrix as recited in claim 6, wherein the overall length of the strip is about 4 inches.

8. The dental matrix as recited in claim 7, wherein the length of said leader is about 1 inch.

9. The dental matrix as recited in claim 5, wherein:
   (a) the width of the strip at said major end portion is about equal to the height of an average human tooth;
   (b) the overall length of the strip is about 4 inches;
   (c) the width of said minor part of the length of the strip is about 1/16 inch; and
   (d) the length of said leader is about 1 inch.

* * * * *